United States Patent [19]

Bogart et al.

[11] Patent Number: 4,786,367

[45] Date of Patent: Nov. 22, 1988

[54] CHEMICALLY TREATED PAPER PRODUCTS—TOWEL AND TISSUE

[75] Inventors: Larry Bogart, Penn Valley; James J. Hipkins, Prospect Park; Nathan A. Edelson, Bala Cynwyd, all of Pa.

[73] Assignee: Scott Paper Company, Philadelphia, Pa.

[21] Appl. No.: 82,110

[22] Filed: Aug. 6, 1987

[51] Int. Cl.⁴ .................................................. D21H 3/12
[52] U.S. Cl. .................................... 162/158; 162/112; 162/135; 162/179; 424/401; 424/443
[58] Field of Search .............. 162/111, 112, 158, 179, 162/135; 424/401, 443; 514/844, 847

[56] References Cited

U.S. PATENT DOCUMENTS

| | | | |
|---|---|---|---|
| 2,137,310 | 11/1938 | Sommer | 162/179 |
| 3,617,439 | 11/1971 | Chapman | 162/158 |
| 4,690,821 | 9/1987 | Smith et al. | 424/401 |

FOREIGN PATENT DOCUMENTS 2260612  9/1974  Fed. Rep. of Germany ...... 162/179

*Primary Examiner*—Peter Chin
*Attorney, Agent, or Firm*—John A. Weygandt; John W. Kane, Jr.

[57] ABSTRACT

Disclosed are soft, absorbent and bulky cellulosic fibrous webs which have been treated so that they impart a soothing or emollient effect to the human skin when used for wiping or drying while essentially retaining their water-absorbent property and strength. The agent used in the present invention is lauroamphoglycinate.

2 Claims, No Drawings

CHEMICALLY TREATED PAPER PRODUCTS—TOWEL AND TISSUE

BACKGROUND OF THE INVENTION

Field of the Invention

This invention relates to soft, absorbent and bulky cellulosic fibrous webs which have been treated so that they impart a soothing or emollient effect to the human skin when used for wiping or drying while essentially retaining their water-absorbent property and strength. The agent used in the present invention is lauroamphoglycinate.

HISTORY OF THE PRIOR ART

It has heretofore been suggested to treat cellulosic fibrous webs with lanolin to impart a feeling of softness to the webs. See, for example, Wemyss, et al., U.S. Pat. No. 2,877,115 and Yang, U.S. Pat. No. 2,944,931 or with other fatty solids, see Britt, U.S. Pat. No. 3,305,392 However, such a treatment has the disadvantage that the water absorbency of the cellulosic web is dramatically reduced by the application of these fatty-type materials, so that the web can no longer satisfactorily perform a wiping or drying function in reference to moist skin.

SUMMARY OF THE INVENTION

The present invention has as its object rather than imparting the feeling of softness to cellulosic webs, the imparting to the human skin an emollient or soothing effect through wiping with a cellulosic web while retaining the drying and strength characteristics of the untreated web. In many environments such as hospitals and clinics, persons are required to frequently wash and dry their hands. This can produce skin irritation, particularly in cold weather. Also, persons suffering from the common cold must frequently apply facial tissues. Also people suffering from diarrhea must use large quantities of toilet tissue. Repeated wipings with treated toilet tissue has been found to condition the perineal region so that it maintains a non-irritating condition. likewise, a soft feeling is achieved after using facial treatment in the manner of this invention so that the nasal skin is left with a velvety soft feeling even after repeated wipes.

The present inventors have found that the water absorbency can essentially be retained while imparting a skin smoothing character to webs for drying or wiping the skin by treating soft absorbent cellulosic webs with a formulation consisting of amphoteric lauroamphoglycinate containing a nonionic surfactant and phosphoric acid. Products made from such webs exhibit the ability to transfer chemicals from the cellulosic fibrous web to the skin generating emollient benefits while concomitantly successfully executing the primary function of the product which is to wipe or dry the skin. Webs treated with lanolin, by contrast, are markedly inferior in producing the desired benefits and are even perceived in some cases as irritating or to cause itching. This may be attributable, not only to the fact that some people are allergic to lanolin, but also as observed by Jacobi, et al., U.S. Pat. No. 3,231,472 dry skin is not caused by the loss of fat material in skin but by the loss of the water soluble constituents therein. In accordance with the present invention, lauroamphoglycinate is applied to a web of cellulosic fibers in an amount from 0.1 to 2% by weight of the web.

Lauroamphoglycinate is the amphoteric organic compound that conforms generally to the formula:

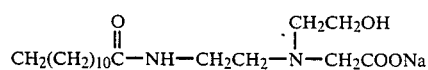

As will be readily appreciated, the fact that the polymers of the present invention are water-soluble totally distinguishes the treatment of the present invention from that of the lanolin treatments of the prior art. Indeed, insofar as the present inventors are aware, lauroamphoglycinate has not been recognized as a skin moisturizer.

DETAILED DESCRIPTION

For the purpose of illustrating the present invention, paper webs having a basis weight of 54 g/m$^2$ (32 pounds per ream of 2,880 square feet) were treated in the finishing process at a point after the paper has been unwound from the parent roll and embossed, but before the slitting, folding, cut off stacking and wrapping processes. The treating fluid, comprising the active ingredients dissolved in water, is applied at a rate to yield the addition of between 0.034 to 1.086 g/m$^2$ (0.02 to 0.64 pounds per ream) of lauroamphoglycinate or 0.1 to 2.0% by weight of the web. For toilet tissue such as Scott COTTONELLE or 2-ply facial, another example illustrating the present invention could be paper webs having basis weight of 27 g/m$^2$ (16 lbs. per ream) of 2,880 square feet were treated at location similar to that disclosed above. The treating fluid comprising the active ingredients dissolved in water is applied at a rate to yield an addition of between 0.017 to 0.543 g/m$^2$ (0.01 to 0.32 lbs./ream of the compound or 0.1 to 2% by weight of web.

Any application technique known in the art which does not unduly compact the web and which evenly distributes the fluid at the desired rate onto the paper web may be employed. These application techniques include spraying, transfer roll coating and gravure printing. If compaction caused by gravure printing is considered too great to the finished product, this step may be carried out prior to the step of bulking by embossing. The amount of compaction which can be suffered is influenced by numerous variables much as the original bulk of the web, consumer expectations regarding bulk and the perceived need for patterned printing which can be achieved by gravure roll methods. The present inventors have found that the benefits perceived by users are best achieved by spraying the treating fluid onto the web. In the examples which follow present inventors employed a method described by them as a doctored kiss roll method. In this process, the path of the paper web is directed over an application roll which rotates in the same direction as the travel of the paper. This roll, which has a smooth surface, for example polished chrome, rotates partially submerged in a bath of the fluid to be applied. As the roll rotates, it picks up a layer of liquid on its surface. The thickness of this layer is determined by the viscosity of the fluid. This layer is then metered to the desired thickness by doctoring the excess off of the roll. The paper, moving faster than the surface of the roll, then wipes the doctored layer of fluid from the roll.

The rate of application for a given paper speed and fluid is controlled by adjustment of the speed of rotation of the coating roll; the angle of wrap (contact with the roll) of the paper over the coating roll; and the type of and setting of the doctor. These adjustments are made as required to deliver the desired quantity of fluid to the web for a given web speed and fluid.

A sheet was prepared as follows:

To paper web having a basis weight of 32.8 pounds per ream of 2880 square feet (55.6 grams per square meter) was applied in the above described manner a quantity of alcolac DV-1995 containing principally lauroamphogylcinate with phosphoric acid and a non-ionic surfactant to yield a lotionized sheet containing 0.64% lauroamphoglycinate by weight of web.

This example illustrates the ability of people to discern differences and benefits from towels treated in accordance with this invention as compared to untreated towels and to appreciate that the functional properties of the treated towels remain unchanged. These products exhibit the ability to transfer chemicals from the cellulosic fibrous web to the skin generating emollient benefits while concomitantly successfully executing the primary function of the product which is to wipe or dry the skin.

The methodology employed involved choosing a panel of normal, healthy individuals and observing whether this panel (which consisted of eleven members) would be able to perceive beneficial differences amongst treated towels and untreated Scott Brand 150 C-fold towels, the towels were presented to the panel with a code number so that the sample identifications were unknown to each panelist. The investigation was carried out privately by each panelist so that there was no interaction with other panelists. Each panelist was to wash their hands with luke warm tap water and a mild liquid soap and then their hands were dried with an untreated towel. The subjects knew specifically that these towels were normal untreated towels and that these towels were utilized as a reference standard. The subjects were then asked to rewash their hands using an identical procedure and this time they were asked to dry their hands with a coded unknown towel. Included amongst the coded samples was a placebo sample containing untreated towel. After the eleven panelists had completed their evaluation, the scores were totaled and are herein shown in the Table I. Each sample was rated on a scale of zero to ten so that the maximum score would have been 110. The panelists were asked to rate the treated and untreated sample with regard to skin benefit.

Besides a subjective functional evaluation of treated verses untreated towel (especially with regard to the key towel properties of strength and absorbency) an objective laboratory test evaluation of the sample was undertaken. These results show that the treated towel remained essentially unchanged in physical properties when compared to the untreated control.

TABLE 1

| Evaluation of Treated Towels | |
| --- | --- |
| Sample Designation | Rating |
| Untreated towel used as placebo | 22 |
| Lauroamphoglycinate | 46 |

This sample clearly shows that the unknown placebo sample is rated significantly lower than either of the treated variants when consiered with respect to skin comfort and functionality.

What is claimed is:

1. A web of cellulosic fibers comprising lauroamphoglycinate in an amount from 0.1 to 2% by weight of the web.

2. A method of simultaneously absorbing water or aqueous body fluids from the human skin while imparting to the skin an emollient effect by wiping the skin with a web of cellulosic fibers comprising lauroamphoglycinate in an amount from 0.1 to 2% by weight of the web.

* * * * *